United States Patent [19]

Meyer

[11] Patent Number: 5,788,487
[45] Date of Patent: Aug. 4, 1998

[54] DENTAL SHIM

[76] Inventor: Alvin Meyer, 20 N. San Mateo Dr. #10, San Mateo, Calif. 94401

[21] Appl. No.: 676,488

[22] Filed: Jul. 8, 1996

[51] Int. Cl.⁶ .................................................. A61C 5/10
[52] U.S. Cl. ............................................................ 433/39
[58] Field of Search ................................ 433/34, 37, 39, 433/40, 41, 44, 47

[56] References Cited

U.S. PATENT DOCUMENTS

| | | |
|---|---|---|
| 1,255,109 | 1/1918 | Russ . |
| 2,217,237 | 10/1940 | Siqveland ........................ 433/39 |
| 2,310,448 | 2/1943 | Leib . |
| 2,538,486 | 1/1951 | Tofflemire ........................ 433/39 |
| 2,594,367 | 4/1952 | Tofflemire . |
| 2,611,182 | 9/1952 | Tofflemire ........................ 433/39 |
| 3,411,214 | 11/1968 | Lazarus . |
| 4,704,087 | 11/1987 | Dragan ............................ 433/39 |
| 5,330,353 | 7/1994 | Wavrin ............................ 433/39 |
| 5,380,198 | 1/1995 | Suhonen ........................... 433/39 |
| 5,425,635 | 6/1995 | Croll .............................. 433/39 |

FOREIGN PATENT DOCUMENTS 3901267   7/1990   Germany .............................. 433/233

*Primary Examiner*—Ralph Lewis
*Attorney, Agent, or Firm*—T. R. Zegree

[57] ABSTRACT

A dental shim insertable between two adjacent teeth adapted in the restoration procedure of a decayed tooth comprises a unitary, flexible metallic body having an arcuate top portion and an arcuate bottom portion. The shim comprises at least one notch in the edge of the top portion thereof to facilitate positioning of the shim between the two teeth and to provide a release of strain induced by adapting the shim to a tooth curvature. The shim may include an apron member formed in the bottom portion and a lining veneer covering the concave surface of its bottom. The shim is easily removable after the tooth restoration is complete.

11 Claims, 1 Drawing Sheet

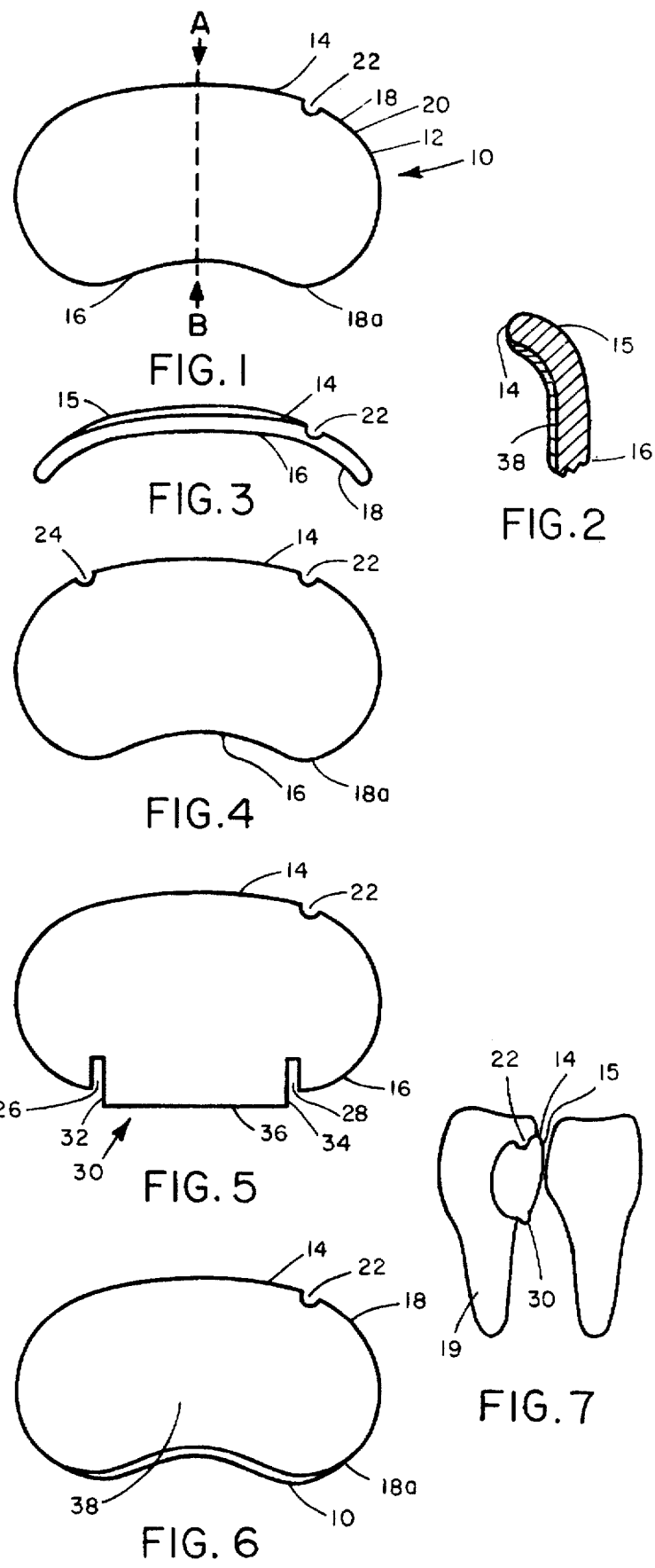

5,788,487

DENTAL SHIM

BACKGROUND OF THE INVENTION

This invention pertains to a dental shim. More particularly, the invention relates to a shim adapted for surrounding the area of a tooth requiring restoration of its lateral surface destroyed by decay.

Various types of matrix bands for use by dentists in the process of filling tooth cavities have been described in the patent literature. For example, U.S. Pat. No. 1,255,109 to Russ describes a matrix band comprising a strip of a material having a transverse slot at one end thereof and lateral ears pressed downwardly over the edges of the band; U.S. Pat. No. 2,310,448 to Leib discloses a narrow thermoplastic ribbon having indentations for use in tensioning around a tooth; U.S. Pat. No. 2,594,367 to Tofflemire describes a matrix band having an aperture through which a filling material may be inserted into a gingival cavity of a tooth; U.S. Pat. No. 3,411,214 to Lazarus covers a unit consisting of a dental band and a closed flattened loop metal bridge embracing the band; U.S. Pat. No. 5,330,353 to Vavrin discloses a dental matrix comprising a plastic member operatively connected to a metal member; and U.S. Pat. No. 5,380,198 to Suhonen describes a dental matrix serving as a framework for inserting fillings into tooth cavities, comprising an opaque metallic coating layered over a transparent material being free of the metallic coating.

While the above-mentioned patents disclose various concepts of dental matrix devices, the present invention provides a new approach to the structure of a shim which offers certain advantages over the prior art matrices.

OBJECTS OF THE INVENTION

In view of the foregoing, it is the principal object of the invention to provide an improved dental shim specifically adapted for use in restoring a tooth having its lateral surface destroyed by decay.

It is another object of the invention to provide a contoured and malleable dental shim adapted for insertion between two adjacent teeth and for easy removal therefrom.

Still another object of the invention is to provide a flexible dental shim comprising a notch in its top margin to mark the position of holding forceps employed during placement of the shim between two adjacent teeth.

Yet another object of this invention is to provide a small dental device, as described herein, which can be manufactured in large quantities at a low cost from readily available materials.

These and other objects of the invention will become more fully apparent from the following description considered in conjunction with the accompanying drawings.

BRIEF SUMMARY OF THE INVENTION

In accordance with the invention described herein in its preferred embodiment, there is provided a small, flexible dental shim adapted to be positioned around a decayed tooth zone to be restored, the shim comprising an elongate strip having an arcuate top edge and an arcuate bottom edge, the top edge including a peripheral notch. The structure of the shim comprises a concave, spheroidal surface between the edge of the top portion and the edge of the bottom portion, the area of such surface extending over about ⅔ of its central area, the remaining ⅓ of said surface being cylindrical.

In another embodiment of the invention, the shim is modified by providing a substantially rectangular apron member extending downwardly in the bottom portion thereof, the apron member being formed by a pair of spaced apart, parallel, sheared vertical cuts.

It is still another embodiment of the invention to provide the surface of the bottom portion of the shim covered with a lining veneer to control adhesion of the applied restorative filling material thereto.

BRIEF DESCRIPTION OF THE DRAWINGS

In the accompanying drawings wherein the reference characters designate corresponding elements throughout the views thereof:

FIG. 1 is a top plan view of the shim showing a notch in the top portion thereof;

FIG. 2 is a cross-sectional view of the shim taken along the line 1–2 of FIG. 1;

FIG. 3 is a side elevational view of the shim shown in FIG. 1;

FIG. 4 is a top plan view of the shim showing a pair of notches in the top edge thereof;

FIG. 5 is a top plan view of the shim illustrating an apron member extending from the bottom portion thereof; and FIG. 6 is a view similar to that of FIG. 1 showing a lining veneer covering the surface of the shim.

FIG. 7 is an elevational view of two adjacent teeth with the shim inserted therebetween.

DETAILED DESCRIPTION OF THE INVENTION

Referring now to the drawings, dental shim 10, as illustrated in FIGS. 1 to 7, is provided in the form of an elongate, small strip 12 designed to wrap a decayed zone of a posterior tooth, thereby generating a mold. The lateral surface of the decayed zone having been damaged requires a restoration by conventional filling of a cleaned tooth cavity with a suitable material, such as silver amalgam alloy, a composite plastic, such as bis GMA or others well known in the art, which usually hardens shortly after application thereof to the tooth cavity. The shim inserted in the space between two adjacent teeth forms a temporary mold for a soft restorative material and retains it while it is hardening to its final form, after which the shim is removed;

Shim 10, which is frequently referred to by dental profession as a matrix, comprises an elongate, thin and flexible strip 12 having an arcuate top margin 14 and an arcuate bottom margin 16 including a pair of distal curved end portions 18 and 18a, respectively.

FIG. 2 illustrates the form of shim 10 in cross-sectional view indicating its spheroidal form 15 at top portion thereof and a cylindrical form 16 at the bottom portion thereof, such two forms representing another important structural feature of the invention.

The body of shim 10 is constructed of all metal, preferably stainless steel, although other metals, such as copper, gold-plated silver or nickel may also be used in its formation. Shim 10 is contoured, malleable and comprises downwardly tapered free ends thus forming an appropriate structure to facilitate the control over the reproduced anatomy of the treated tooth in providing a naturally configured restoration.

Shim 10 is made in a small size, generally about ½ inch long and about ¼ inch wide by punching from a metallic sheet stock, such as stainless steel formula 305 of about 0.0015 to 0.002 inch thickness. However, the size and the thickness of the shim may vary to some extent as may be required for a specific restoration of a tooth to reproduce its natural anatomy.

It is one of the important features of the invention that shim 10 comprises notch 22 disposed inwardly from edge 20 of top portion 14, the purpose of which is to define the edge of shim 10 for its placement close to the biting surface of the tooth and to facilitate a correct positioning of a carrying instrument employed during the restoration procedure, such as forceps, in order to provide an engagement of shim 10 with the tooth. While notch 22 illustrated in FIGS. 1 and 4-6 is of a substantially circular configuration, it may also be a V-shaped, oval or rectangular form. Notch 22 is preferably positioned a short distance from curved end 18 of shim 10. If desired, second notch 24 of a similar configuration may be provided in the opposite portion of edge 20, as shown in FIG. 4, to further facilitate the procedure of tooth restoration using shim 10. Moreover, even more notches may be provided in the same edge.

When shim 10 is inserted between two adjacent teeth and fitted snugly therebetween, notch 22 provides an area where it releases a portion of its stress while in a surrounding position around a tooth.

It is another important feature of this invention to provide a pair of spaced apart, parallel, sheared, vertical cuts 26 and 28 in the central area of bottom portion 16, forming a substantially rectangular apron member 30 protruding downwardly somewhat below the edge of bottom portion 16 of shim 10. Apron member 30 comprises a pair of parallel, vertically disposed edges 32 and 34 and a straight horizontal edge 36 therebetween, as shown in FIG. 5. The three free edges 32, 34 and 36 of apron member 30 facilitate producing apron member 30 of a controlled length as may be required and permit apron member 30 to be burnished to an irregularly shaped root of a tooth.

The main usefulness of apron member 30 is to cover the decayed portion of a tooth to be filled after the decay has been cleaned. Furthermore, apron member 30 provides an intimate adaptation to the surface of a tooth root when the root surface does not lie in the same plane as the coronal surface of the restoration.

It is still another embodiment of the present invention to provide lining veneer 38 in various forms for covering the surface of shim 10, thereby controlling adherence between the applied restorative composition and the surface of shim 10. Lining veneer 38, illustrated in FIG. 6, may be formed from a coating of a polymeric material, such as polyethylene or Teflon. Lining veneer 38 is firmly attached to the surface of shim 10, but readily removable therefrom. In another type of covering, lining veneer 38 may be in the form of a synthetic film, such as a pigmented resin film which is loosely attached over the concave surface of the tooth cavity which coheres with the restorative composition to form a smooth surface of a tooth-matching color. In still another application, lining veneer 38 may be applied in the form of a coating of a lubricant material, such as a silicone wax, which will prevent the tooth filling composition from adhering to concave surface 16 of shim 10.

It will be understood that any of the above-described lining veneers will perform very satisfactorily in the selected procedure for filling a prepared tooth cavity by a dentist.

It will be apparent from the foregoing description which characterizes the various features of the invention by providing specific examples of its embodiments that I have devised a novel, structurally simple unitary dental shim especially adapted as an aid in the restoration of a tooth by filling a prepared cavity with a suitable composition. When the flexible, metallic shim according to the invention is placed in operative position by its engagement with the outer surface of a tooth to be treated, the procedure of restoration is simplified and facilitated in achieving the desired result, i. e. the provision of the surface of a tooth resembling its original contour.

In view of simplicity of its design and availability of materials required for its construction as a one-piece unit, the shim of this invention may be produced inexpensively in large volume.

It will be understood that changes and modifications in the form or in the constructional details of my invention as herein described may be made without departing from the spirit thereof or the scope of the claims which follow.

I claim:

1. A flexible dental shim adapted to be positioned around a decayed tooth zone to be restored, comprising:

an elongated strip having first and second ends, a curved top edge, and a bottom edge; said top edge extending from said first end to said second end and curving downward from the middle of the top edge to said first end and said second end; said bottom edge extending from said first end to said second end; said first and second ends each having a curved edge extending between said top edge and said bottom edge;

said elongated strip further including an inner surface defined by said top edge, said bottom edge, and said first and second end edges for positioning around the decayed tooth zone and an outer surface on the side of said strip opposite said inner surface;

said elongated strip having an arcuate top portion that includes said top edge and curves inward toward said inner surface, said top portion including a notch in said top edge thereof; said elongated strip further having end portions adjacent said first and second end edges that curve inward toward said inner surface; said inward curves of said top portion and said end portions producing a concave shape for said inner surface.

2. A shim of claim 1 wherein the inner surface thereof between said top portion and said bottom edge is spheroidal extending over about ⅔ of a central area of said shim and the remaining ⅓ of said central area is cylindrical.

3. A shim of claim 1 wherein said strip is made of metal.

4. A shim of claim 3 wherein said metal comprises stainless steel.

5. A shim of claim 1 wherein said top portion includes a second notch in said top edge.

6. A shim of claim 1 wherein said bottom edge comprises a pair of spaced apart, parallel, sheared vertical cuts in a central area of said bottom edge forming an apron member extending downwardly.

7. A shim of claim 6 wherein said apron member comprises a pair of parallel vertical edges formed by said vertical cuts and a horizontal edge therebetween.

8. A shim of claim 7 wherein said horizontal edge forms the bottom edge of said shim.

9. A shim of claim 1 wherein said inner surface includes a lining veneer in the form of a coating firmly adhering to the inner surface of said shim.

10. A shim of claim 1 wherein said inner surface includes a lining veneer in the form of a loosely attached synthetic film.

11. A shim of claim 1 wherein said inner surface includes a lining veneer in the form of a lubricant material.

* * * * *